United States Patent [19]
Carter et al.

[11] Patent Number: 5,203,766
[45] Date of Patent: Apr. 20, 1993

[54] WRIST BRACE

[75] Inventors: Peter R. Carter, Dallas, Tex.; John C. Gates, Fountain Valley; Edward L. Castillo, Laguna Hills, both of Calif.

[73] Assignee: Innovation Sports, Inc., Irvine, Calif.

[21] Appl. No.: 710,359

[22] Filed: Jun. 3, 1991

[51] Int. Cl.⁵ ............................................. A61F 5/00
[52] U.S. Cl. ........................................ 602/21; 602/16
[58] Field of Search ............... 128/26, 77, 87 R, 878; 602/5, 16, 20, 21; 623/57, 61-62

[56] References Cited

U.S. PATENT DOCUMENTS

2,438,144  7/1945  Bunyar, Jr. .
4,384,571  5/1983  Nuzzo et al. .
4,809,688  3/1989  Aymerica del Valle et al. .
5,002,044  3/1991  Carter .

Primary Examiner—Richard J. Apley
Assistant Examiner—Linda C. M. Dvorak
Attorney, Agent, or Firm—Stetina and Brunda

[57] ABSTRACT

A brace for supporting a wrist is disclosed which is specifically adapted to allow controlled regulated movement of the wrist during a healing process. The brace is formed by an anterior forearm plate which has a pair of elongate struts attached thereto. A hand brace is pivotally connected to the struts in a manner wherein the amount of pivotal movement of the hand brace may be controlled through the manipulation of a plurality of stop members which extend between the hand brace and the struts. The hand brace is further used to apply downward pressure to the posterior aspect of the user's hand to aid in the healing process. Such pressure is constantly maintained though pivotal movement of the wrist is permitted by the hand brace. A posterior forearm plate is releasably attached to the struts and is used to maintain the wrist brace upon the user's forearm. The wrist brace further includes a palm plate which is attached to the hand brace and is operable to selectively apply upward pressure to the palmar surface of the user's hand.

20 Claims, 6 Drawing Sheets

WRIST BRACE

FIELD OF THE INVENTION

The present invention relates to braces for supporting joints, and more particularly to a wrist brace specifically adapted to correct wrist misalignment while permitting regulated movement of the wrist.

BACKGROUND OF THE INVENTION

As is well known, the wrist joint comprises a plurality of bones disposed between the radius and metacarpal bones of the arm. One of the most common types of fractures occurring in humans is a distal radial fracture, i.e. a fracture of the lower end of the radius, which is commonly known as a Colles' fracture. Medical studies have indicated that patients suffering from distal radial fractures are oftentimes subjected to a persistent disability which lingers despite the healing of the radius. This disability is often attributed to a failure to restore a proper anatomical orientation between the capitate bone of the wrist and the radius after such bones have become malaligned due to the fracture. In addition to fractures of the distal radius, malalignment between the capitate bone and radius has also been attributed to intercalary arpal instability or sub-luxation due to wrist ligament injury.

The use of casts to immobilize injured joints and the use of external braces to provide support to and limit the movement of joints is well known. Recent advancements in the rehabilitation of joint injuries have led to the realization that early active motion of an injured joint following surgery or other trauma is essential to an expedited and complete healing process.

To correct malalignment of the hand or forearm due to distal radial fractures, intercalary carpal instability or wrist ligament injury, it is generally necessary to exert upward or downward pressure on the hand so as to cause a volar or dorsal transrelocation of the distal carpal row and hand to their proper alignment on the forearm bone. When this is accomplished, the intercalary segment (proximal carpal row) is also properly aligned. Though many types of wrist braces are currently known in the prior art, the majority of such wrist braces possess certain inherent deficiencies which detract from their overall utility. Foremost of these deficiencies is the general inability of such wrist braces to exert the necessary pressure on the hand to achieve a volar or dorsal transrelocation while allowing graded active motion of the capitate bone about a single axis relative the radius. As previously indicated, such early active motion of the wrist joint is essential in facilitating a proper and complete healing process. As such, there exists a substantial need in the art for a wrist brace which overcomes these and other deficiencies associated with the prior art. Importantly, both volar and dorsal malalignment of the hand on the forearm can be corrected by the wrist brace constructed in accordance with the present invention.

SUMMARY OF THE INVENTION

In accordance with the preferred embodiment of the present invention there is provided a wrist brace generally comprising an anterior forearm plate positionable adjacent the anterior aspect of the user's forearm. Lateral and medial struts are attached to the anterior forearm plate so as to be positioned adjacent the lateral and medial aspects of the forearm, respectively. Pivotally connected to the proximal ends of the lateral and medial struts is a hand brace portion which is positioned adjacent the posterior selectively apply downward pressure to the second and third metacarpal bones of the user's hand when attached to the lateral and medial struts. In the preferred embodiment, the pivotal connection between the hand brace and struts facilitates controlled pivotal movement of the user's wrist about a single axis. The wrist brace further comprises a posterior forearm plate which is positioned adjacent the attachable to the lateral and medial struts for purposes of maintaining the wrist brace upon the user's forearm.

The wrist brace further comprises a means associated with the lateral and medial struts for adjusting the distance separating the lateral strut from the medial strut as well as the distance separating the struts from the anterior forearm plate. Such an adjustment feature is provided to insure that the struts may be properly positioned relative the lateral and medial aspects of the forearm when the brace is attached thereto. Additionally, the adjustment feature allows the hand brace to be abutted against the posterior aspect of the user's hand so as to apply the aforementioned downward pressure to the posterior aspect of the user's hand and more particularly, the second and third metacarpal bones. In the preferred embodiment, the adjusting means comprises first and second pairs of elongate threaded members which extend through and interconnect the anterior forearm plate and the struts in a manner wherein the struts are selectively positionable along the length of the threaded members. Importantly, the threaded members extend through pairs of elongate grooves disposed within the anterior forearm plate so as to be adjustable both inwardly and outwardly relative the forearm.

The hand brace portion of the present invention comprises a lateral member having a lateral extension formed thereon which is slidably connected to a medial member having a medial extension formed thereon. When the lateral and medial members are interconnected, the lateral and medial extensions overlap the proximal ends of the lateral and medial struts, respectively. Advantageously, the slidable connection between the lateral and medial members allows the distance separating the lateral and medial extensions to be adjusted so as to coincide with adjustments made to the distance separating the struts.

The pivotal connection between the hand brace portion and the struts is facilitated by a pair of pivot pins. The wrist brace is preferably attached to the user's hand such that the pivot pins are disposed laterally on opposite sides of the capitate bone of the user's wrist. In the preferred embodiment, the pivot pins are constructed from a radiopaque material so that the pins may be identified in imaging applications such as an x-ray.

The wrist brace of the present invention further comprises a palm plate which is releasably attached to the hand brace portion and positioned adjacent the palmar surface of the user's hand. Also included is an adapter pad which is releasably attached to the hand brace and used to provide a firm padded interface between the hand brace and the posterior aspect of the user's hand.

In accordance with a second embodiment of the present invention, there is provided a wrist brace which comprises an anterior forearm plate having a generally semi-circular configuration and including lateral and medial struts rigidly attached thereto. Lateral and medial connectors are slidably interfaced to the lateral and medial struts via first and second adjustment members which are operable to selectively position the lateral and medial connectors relative the struts. Such positioning is used to properly align the connectors relative the lateral and medial aspects of the user's wrist. A hand brace portion having a configuration substantially identical to that as included in the first embodiment is pivotally connected to the lateral and medial connectors and adapted to selectively apply downward pressure to the second and third metacarpal bones of the user's hand. The wrist brace of the second embodiment further comprises a palm plate attached to the hand brace in a manner wherein the palm plate is selectively operable to apply upward pressure to the palmar surface of the user's hand.

It is an object of the present invention to provide a wrist brace which causes a volar or dorsal transrelocation of the bones of the hand and wrist as needed to correct a malalignment of the hand or the forearm due to fracture of the distal radius, intercalary carpal instability, or subluxation due to wrist ligament injury.

Another object of the present invention is to provide a wrist brace which permits graded active motion around the capitate bone of the wrist while causing a volar or dorsal transrelocation.

BRIEF DESCRIPTION OF THE DRAWINGS

These as well as other features of the present invention will become more apparent upon reference to the drawings wherein.

DETAILED DESCRIPTION OF THE PREFERRED EMBODIMENT

The description set forth below in connection with appended drawings is intended merely as a description of presently preferred embodiments of the invention, and is not intended to represent the only form in which the present invention may be utilized. The description sets forth the functions and structural elements of the invention in connection with the illustrated preferred embodiments. It will be understood however that the same or equivalent functions and advantages of the present invention may be accomplished by different embodiments which are encompassed within the spirit and scope of the present invention.

Figure 1:
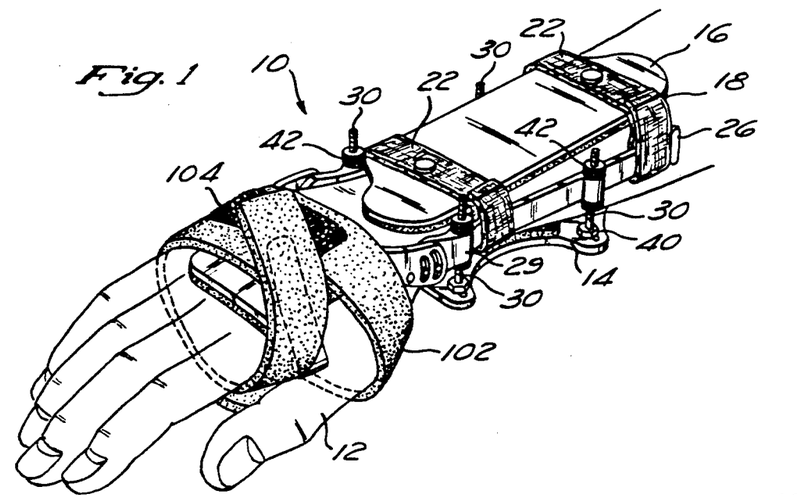
FIG. 1 is a perspective view of the wrist brace constructed in accordance with a first embodiment of the present invention as attached to the arm of a user.
Figure 2:
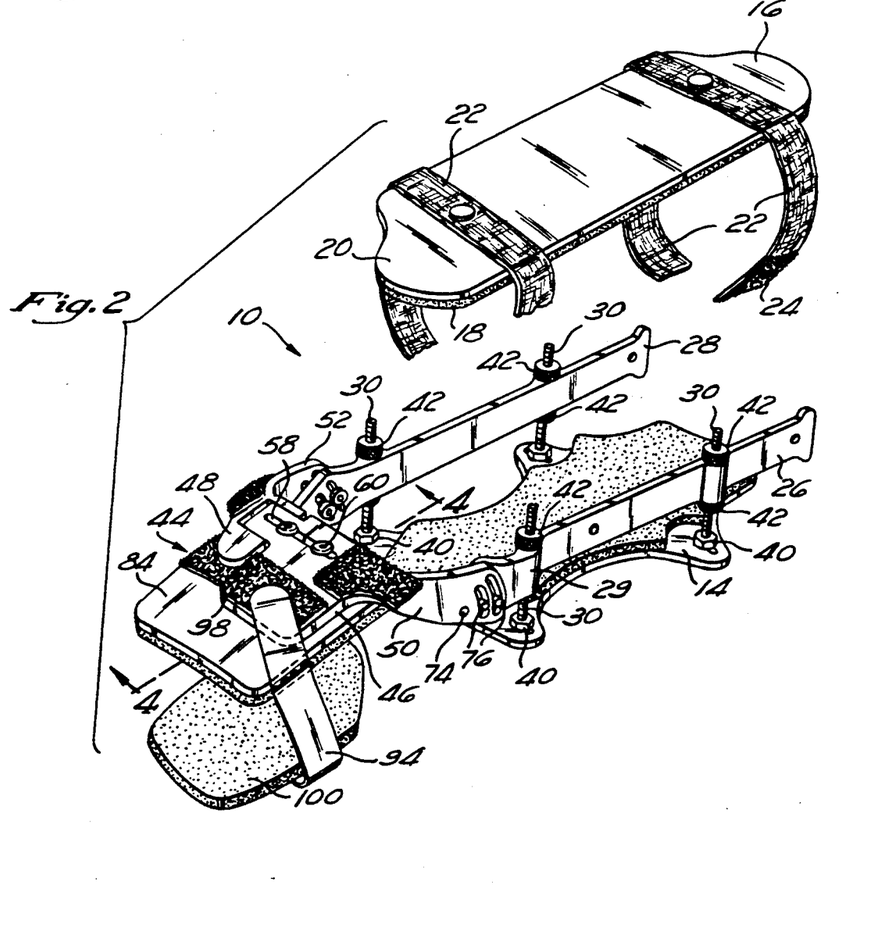
FIG. 2 is a perspective view illustrating the components comprising the first embodiment of the present invention.
Figure 3:
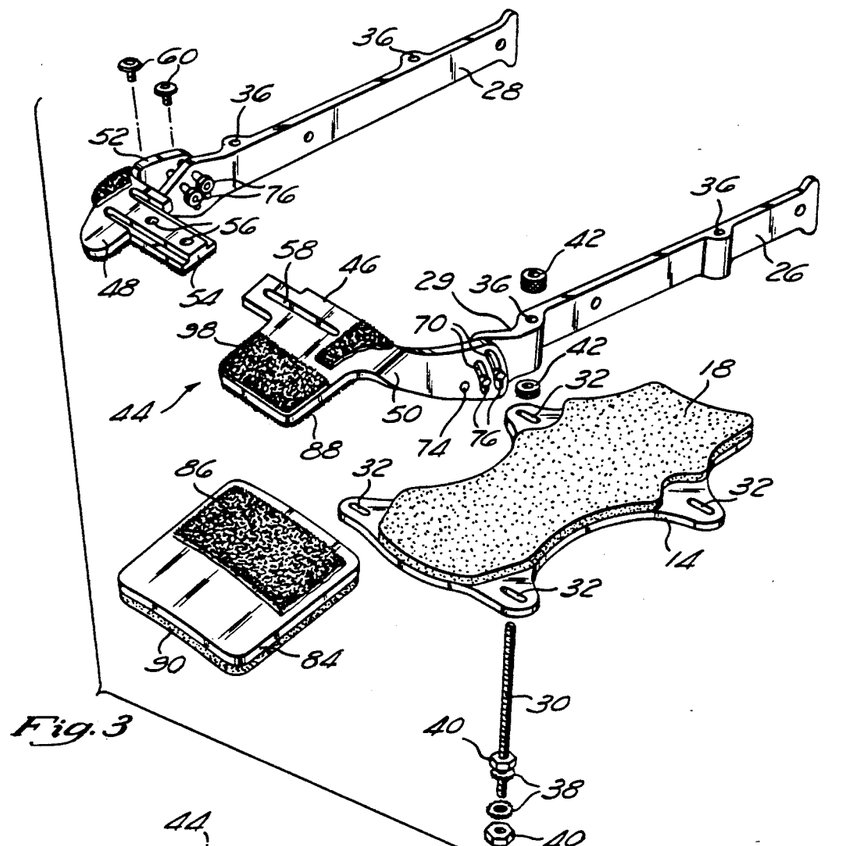
FIG. 3 is an exploded view illustrating the manner in which the hand brace, anterior forearm plate, and struts of the first embodiment are interfaced.

Referring now to the drawings, the wrist brace 10 constructed in accordance with a first embodiment of the present invention is depicted. For purposes of illustration, the wrist brace 10 is illustrated in a right-arm and hand embodiment which is adapted to be worn upon the right hand 12 of a user. However, it will be recognized that the invention is additionally applicable to left-hand embodiments with the structure of the brace 10 being the same but reversed in orientation. As best shown in FIGS. 1-3, the wrist brace 10 is composed of an anterior forearm plate 14 and a posterior forearm plate 16. The anterior forearm plate 14 and posterior forearm plate 16 each have an elongate, generally planar configuration and are positionable on opposite sides of the arm of the user. In this respect, when wearing the brace 10, anterior plate 14 is positioned adjacent the anterior aspect of the user's forearm while posterior plate 16 is positioned adjacent the posterior aspect of the user's forearm. In the preferred embodiment, anterior plate 14 and posterior plate 16 are formed from a plastic material having sufficient rigidity to withstand impact forces yet be sufficiently light in weight so as not to overly impair movement of the user's arm. However, other materials possessing sufficient strength and rigidity are contemplated herein. Attached to the inner forearm-contacting surfaces of anterior plate 14 and posterior plate 16 are layers of foam padding 18 which are used to alleviate discomfort to the user when wearing the wrist brace 10. Posterior plate 16 further includes a generally arcuate proximal extension 20 formed thereon which is preferably positioned above the distal end of the radius of the patient. The attachment of posterior plate 16 to the user's arm is facilitated by a plurality of strap members 22 attached to posterior plate 16, each of which include a velcro portion 24 thereon. The manner in which strap members 22 are utilized will be explained below.

Wrist brace 10 of the present invention further includes a lateral strut 26 and a medial strut 28. Lateral strut 26 and medial strut 28 each have an elongate configuration and are positionable on opposite sides of the forearm of a user. When brace 10 is worn by a user, lateral strut 26 is positioned adjacent the lateral aspect of the forearm and medial strut 28 is positioned adjacent the medial aspect of the forearm. In the preferred embodiment, lateral strut 26 and medial strut 28 are formed from a plastic material which, like anterior plate 14 and posterior plate 16, is adapted to possess strength and rigidity yet be light in weight. Additionally, other materials possessing like characteristics are also contemplated herein. Advantageously, lateral strut 26 is formed to include an offset 29 which is adapted to clear the trapezium and scaphoid bones of the user's hand 12 when brace 10 is attached thereto. As best seen in FIGS. 2 and 3, lateral strut 26 and medial strut 28 are attached to anterior forearm plate 14 via a plurality of elongate threaded members 30. Each of threaded members 30 is preferably formed of plastic and extends through one of the four elongate grooves 32 laterally disposed within anterior plate 14. After extending through grooves 32, a first pair of threaded members 30 are received into and extend through a first set of apertures 34 disposed within lateral strut 26. Similarly, a second pair of threaded members 30 are received into and extend through a second set of apertures 36 disposed within medial strut 28. Threaded members 30 are secured within grooves 32 through the utilization of lock washers 38 and nuts 40 which are threadably received onto threaded members 30. As will be recognized, the extent to which threaded members 30 protrude from anterior plate 14 is dependent upon the positioning of lock washers 38 and nuts 40 along the length of threaded members 30. Additionally, due to the receipt of threaded members 30 into elongate grooves 32, the relative positioning of each of threaded members 30 may be adjusted inwardly or outwardly relative the user's forearm.

Lateral strut 26 and medial strut 28 are positioned and secured upon threaded members 30 through the manipulation of pairs of knurl nuts 42 which are threadably interfaced to threaded members 30. As can be appreciated, by adjusting the positions of knurl nuts 42 along the length of threaded members 30, lateral struts 26 and medial strut 28 are themselves selectively positionable along the length of threaded members 30. Thus, the distance separating lateral strut 26 from medial strut 28 may be adjusted by sliding the threaded members 30 within grooves 32, while the distance separating lateral strut 26 and/or medial strut 28 from anterior forearm plate 14 may be adjusted by selectively positioning lateral strut 26 and/or medial strut 28 on threaded members 30. As will be recognized, the aforementioned adjustability of lateral strut 26 and medial strut 28 is desired to permit wrist brace 10 to be specifically sized in accordance with the anatomical requirements of a particular user. Additionally, the adjustability of lateral strut 26 and medial strut 28 relative anterior forearm plate 14 is used to apply downward pressure to the posterior aspect of the user's hand in a manner which will be discussed below. As best seen in FIG. 1, posterior plate 16 is attached to anterior plate 14 by wrapping the opposed ends of each of the strap members 22 about lateral strut 26 and medial strut 28, respectively, thereby creating a firm interface of anterior plate 14, posterior plate 16, and struts 26 and 28 to the user's forearm. The strap members 22 are maintained in a wrapped orientation about lateral strut 26 and medial strut 28 via the velcro portions 24 included thereon.

Figure 4:
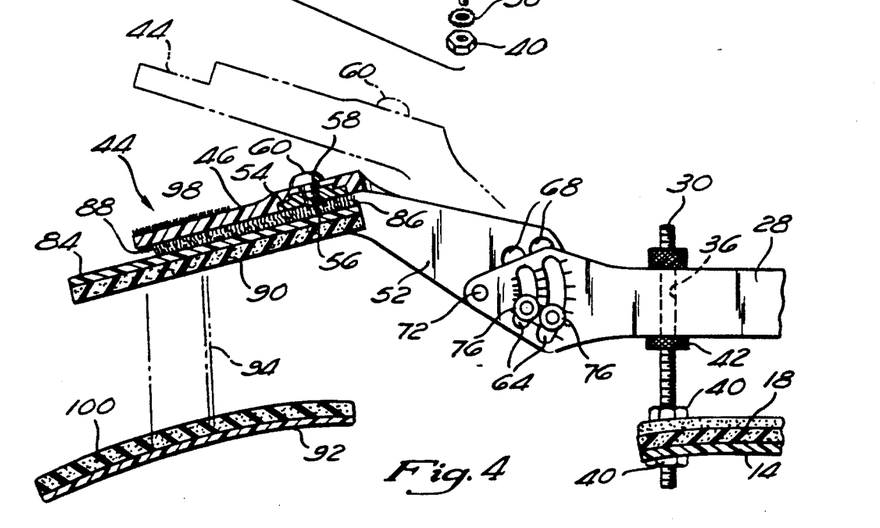
FIG. 4 is a cross-sectional view taken along line 4—4 of FIG. 2, further illustrating the range of motion of the hand brace of the first embodiment.

Pivotally connected to the proximal ends of lateral strut 26 and medial strut 28 is a hand brace portion 44. When brace 10 is attached to a user's arm, hand brace 44 is positioned adjacent the posterior aspect of the user's hand 12. In the preferred embodiment, hand brace 44 is composed of a lateral member 46 and a medial member 48. Lateral member 46 is formed to include a lateral extension 50 thereon while medial member 48 is formed to include a medial extension 52 thereon. Medial member 48 is preferably slidably connected to lateral member 46 through the receipt of a T-shaped projection 54 formed on medial member 48 into a correspondingly shaped recess (not shown) formed within lateral member 46. Disposed within projection 54 of medial member 48 are a pair of internally threaded apertures 56 while disposed within lateral member 46 is an elongate slot 58. As best seen in FIG. 4, when lateral member 46 is slidably connected to medial member 48, apertures 56 are coaxially aligned with elongate slot 58. In this respect, the receipt of fasteners, such as screws 60, into slot 58 and subsequently into apertures 56 is operable to rigidly secure lateral member 46 to medial member 48. Additionally, due to the receipt of screws 60 into slot 58, the distance separating lateral extension 50 from medial extension 52 may be adjusted so as to coincide with adjustments made to the distance separating struts 26 and 28.

Figure 5:
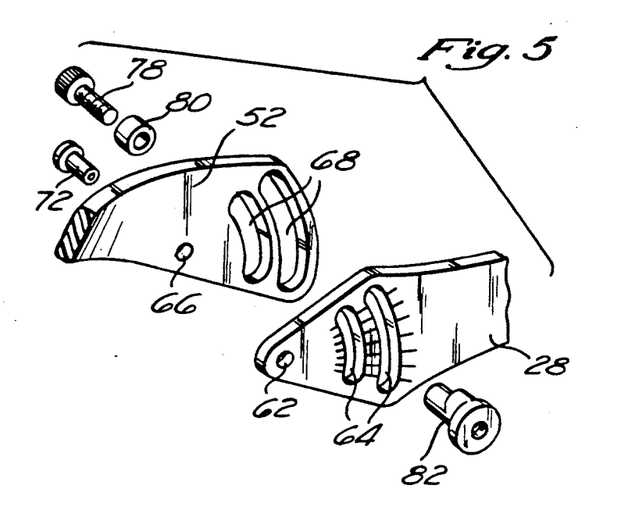
FIG. 5 is an exploded view illustrating the manner in which the hand brace is interfaced to a strut of the first embodiment.

Referring now to FIGS. 3-5, disposed within the proximal end of medial strut 28 is an aperture 62 and a first pair of arcuate slots 64. Though not shown, the proximal end of lateral strut 26 includes an aperture and a second pair of arcuate slots disposed therein which are oriented in a configuration identical to that as shown with respect to aperture 62 and arcuate slots 64 of medial strut 28. Disposed within medial extension 52 is an aperture 66 and a third pair of arcuate slots 68, while disposed within lateral extension 50 is an aperture (not shown) and a fourth pair of arcuate slots 70 which are oriented in a configuration identical to aperture 66 and arcuate slots 68 of medial extension 52. In the preferred embodiment, medial member 48, is attached to medial strut 28 through the receipt of a first pivot pin 72 into the coaxially aligned apertures 62 and 66. Similarly, the attachment of lateral member 46 to lateral strut 26 is facilitated by the receipt of a second pivot pin 74 into the coaxially aligned apertures disposed within lateral strut 26 and lateral member 46. When lateral strut 26 is connected to lateral member 46, arcuate slots 70 are generally aligned with the arcuate slots disposed within lateral strut 26. Additionally, when medial strut 28 is attached to medial member 48, arcuate slots 64 are generally aligned with arcuate slots 68.

Figure 8:
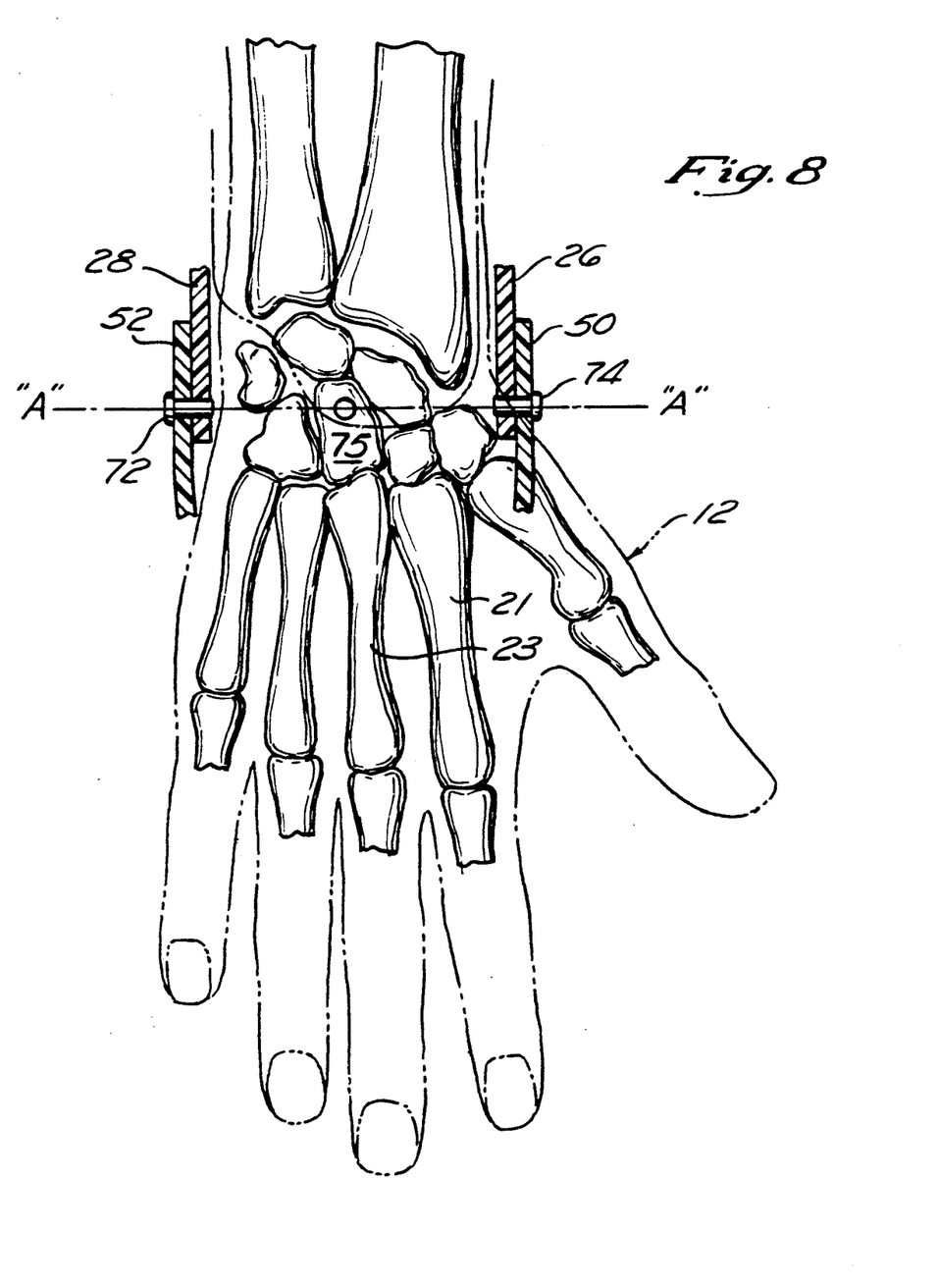
FIG. 8 is a top view of a user's hand, illustrating the manner in which the pivot pins of the first embodiment are positioned laterally adjacent the capitate bone of the user's wrist.

As will be recognized, the pivotal connection between hand brace 44 and struts 26 and 28 is facilitated by first pivot pin 72 and second pivot pin 74. As seen in FIG. 8, since the capitate bone 75 of the wrist serves as the primary pivot point, in order for wrist brace 10 to function properly, it is essential that pivot pins 72 and 74 be positioned on an axis "A" extending laterally through capitate bone 75 so as to be disposed laterally on opposite sides of the capitate bone 75. To verify that such alignment has been achieved, pivot pins 72 and 74 are constructed from a radiopaque material so as to be identifiable in x-ray imaging. As previously indicated, the distance separating lateral strut 26 from medial strut 28 may be increased or decreased by adjusting the positions of threaded members 30 within elongate grooves 32 of anterior plate 14. Because hand brace 44 is pivotally connected to struts 26 and 28, the distance separating lateral member 46 from medial member 48 of hand brace 44 must be adjusted a distance corresponding to the desired increase or decrease separating struts 26 and 28. As also previously indicated, such adjustment is facilitated by the slidable receipt of T-shaped projection 54 into the corresponding recess disposed within lateral member 46. Thus, by loosening screws 60, lateral member 46 may be moved concurrently with lateral strut 26 and medial member 48 may be moved concurrently with medial strut 28. In the preferred embodiment, both lateral member 46 and medial member 48 are constructed from plastic, though it will be appreciated that other materials may be utilized as an alternative.

Referring now to FIGS. 4 and 5, the degree of pivotal movement between hand brace 44 and struts 26 and 28 is controlled by a plurality of stop members 76. In the preferred embodiment, each of stop members 76 comprises a fastener, such as a screw 78, which is initially received into a cylindrical bushing 80 and subsequently into an internally threaded lock member 82. A first pair of stop members 76 are received into the aligned pairs of arcuate slots 64 and 68 while a second pair of stop members 76 are received into the arcuate slots 70 which are aligned with the arcuate slots disposed within the proximal end of lateral strut 26. When stop members 76 are positioned within the respective pairs of aligned slots, hand brace 44 is movable in the manner shown in FIG. 4. As can be appreciated, by adjusting the relative positioning of stop members 76 within the aligned slot pairs, the movement of hand brace 44 may be controlled, i.e. limited. In this respect, one stop member comprising each pair may be positioned so as to limit wrist extension while the other stop member comprising the pair may be positioned to limit wrist flexion.

As best seen in FIGS. 3 and 4, attached to the inner, hand-contacting surface of hand brace 44 is an adaptor pad 84 which is used to provide a firm padded interface between hand brace 44 and the posterior aspect of the user's hand. Adaptor pad 84 includes a velcro patch 86 disposed on the outer surface thereof which is used to releasably attach adaptor pad 84 to a velcro patch 88 disposed on the inner surface of hand brace 44. Adaptor pad 84 further includes a layer of cushioning material 90 attached to the bottom surface thereof to alleviate any discomfort or irritation to the user's hand 12.

Figure 6:
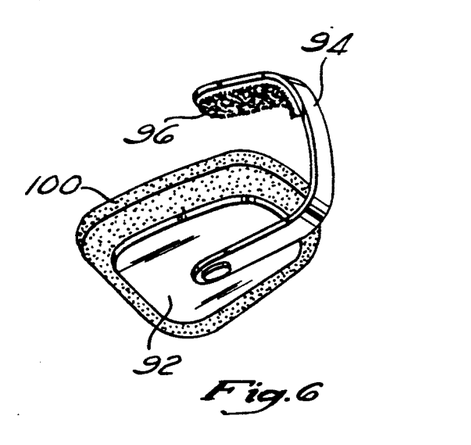
FIG. 6 is a perspective view of the palm plate of the first embodiment.
Figure 7:
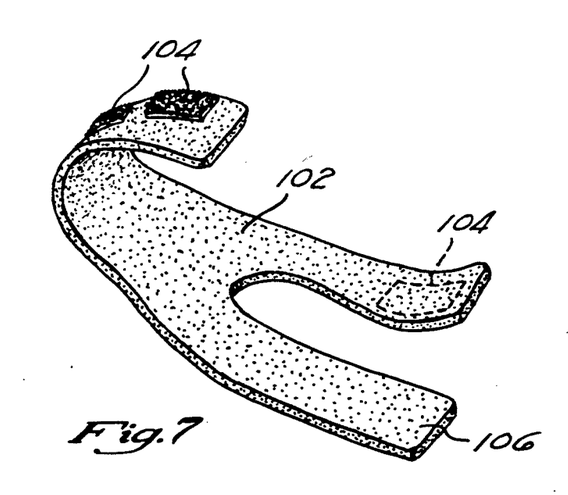
FIG. 7 is a perspective view of a belt member used to maintain the palm plate in abutting contact with the hand brace of the first embodiment.

Referring now to FIG. 6, the wrist brace 10 of the present invention further includes a palm plate 92 which is positioned adjacent the palmar surface of the user's hand. In the preferred embodiment, palm plate 92 includes a bracket 94 attached thereto which is used to facilitate the attachment of palm plate 92 to hand brace 44 in the manner shown in FIG. 2. In this regard, bracket 94 includes a velcro portion 96 which is releasably attached to a velcro patch 98 disposed on the top surface of hand brace 44, and more particularly lateral member 46. Palm plate 92 further includes a layer of cushioning material 100 attached thereto to provide a padded interface between palm plate 92 and the palmar surface of the user's hand. As seen in FIG. 7, a belt member 102 which is constructed from a pliable material is provided to maintain palm plate 92 in attachment to hand-brace 44 and to maintain hand brace 44 in firm contact with the posterior aspect of the user's hand 12. Belt member 102, which includes velcro patches 104, is interfaced to palm plate 92 and hand brace 44 in the manner shown in FIG. 1. Particularly, belt member 102 extends about the hand 12 of the user with the extension 106 formed thereon extending between the thumb and index finger of the user.

With the structure defined the operation of the wrist brace 10 of the present invention may be described. Initially, the anterior forearm plate 14 is positioned adjacent the anterior aspect of the user's forearm and the user's hand 12 is positioned such that the hand brace 44 is positioned adjacent the posterior aspect of the hand 12. Importantly, as such positioning of the anterior forearm plate 14 and hand brace 44 occurs, the stop members 76 are tightened so as to maintain hand brace 44 in a fixed, i.e. "neutral", position which is generally parallel the posterior aspect of the user's hand. The lateral strut 26 and medial strut 28 are then adjusted so as to be positioned against the lateral and medial aspects of the user's forearm. Particularly, the distance separating the struts 26 and 28 is increased or decreased by loosening the nuts 40 and sliding the threaded members 30 within the grooves 32 disposed within anterior plate 14. In any instance when the distance separating lateral strut 26 from medial strut 28 is being adjusted, the screws 60 used to rigidly secure lateral member 46 to medial member 48 of hand brace 44 are loosened so as to permit the lateral member 46 and medial member 48 to slide relative to one another a distance coinciding with the distance adjustments being made between the struts 26 and 28. When struts 26 and 28 are properly positioned, the nuts 40 are tightened down to maintain the threaded members 30 in the proper orientation and the screws 60 are tightened to maintain the lateral member 46 and medial member 48 in the proper orientation. Additionally, the distance separating the struts 26 and 28 from the anterior plate 14 is adjusted by loosening knurl nuts 42 and positioning the struts 26 and 28 in a desired location along the length of threaded members 30 so as to be substantially centered between the anterior and posterior aspects of the user's arm.

Figures 16, 17:
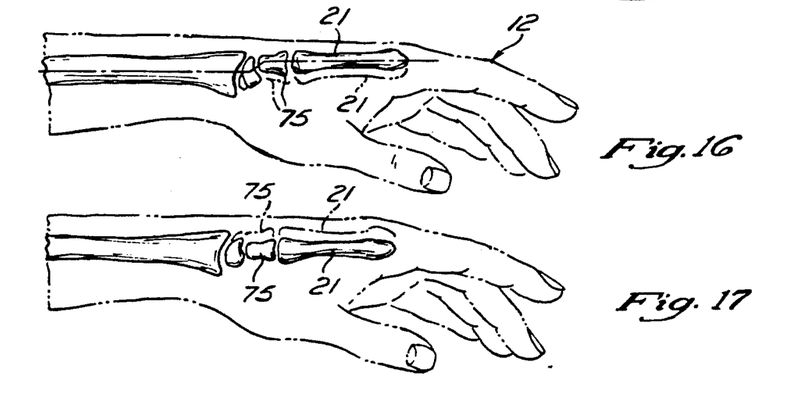
FIG. 16 is a side view of a user's hand, illustrating the positions of the bones of the forearm, wrist, and hand wherein a volar transrelocation is required to achieve proper alignment.
FIG. 17 is a side view of a user's hand, illustrating the positions of the bones of the forearm, wrist, and hand wherein a dorsal transrelocation is required to achieve proper alignment.

After the anterior plate 14 and struts 26 and 28 have been positioned user's forearm, the posterior forearm plate 16 is attached to the struts 26 and 28 to maintain the wrist brace 10 on the user's forearm. Particularly, the strap members 22 are wrapped about struts 26 and 28 and maintained in attachment through the use of the velcro portions 24 contained thereon. Posterior plate 16 is oriented such that the arcuate extension 20 formed thereon is positioned above the distal end of the radius of the user. Once wrist brace 10 has been secured to the user's forearm, the hand brace 44 is caused to apply downward pressure to the second metacarpal bone 21 and third metacarpal bone 23 of the user's hand 12 (shown in FIG. 8). In the preferred embodiment, the application of such pressure is facilitated by moving lateral strut 26 and medial strut 28 downwardly along the length of threaded members 30 toward anterior plate 14. As previously specified, hand brace 44 is initially fixed in a neutral position. Thus, by moving lateral strut 26 and medial strut 28 toward anterior plate 14, hand brace 44 is abutted against the posterior aspect of the user's hand in a manner operable to apply the aforementioned downward pressure. Such downward pressure is necessary for purposes of causing a volar transrelocation to correct a malalignment of the bones of the user's hand, wrist, and forearm, as seen in FIG. 16.

When anterior plate 14 and struts 26 and 28 are properly positioned about the forearm of the user, the first pivot pin 72 and second pivot pin 74 will preferably be disposed on opposite sides of the capitate bone 75 of the wrist of the user. As previously indicated, the first pivot pin 72 and second pivot pin 74 are constructed of a radiopaque material so as to be identifiable in an x-ray. As such, to insure that pivot pins 72 and 74 are properly positioned adjacent the capitate bone 75, an x-ray of the user's hand is taken to insure that the proper positioning of pivot pins 72 and 74 has been achieved. If the pins 72 and 74 are not properly positioned, the anterior plate 14 and struts 26 and 28 are repositioned on the forearm of the user and another x-ray taken to check the positioning of the pivot pins 72 and 74. This particular process is repeated until the proper orientation of the pivot pins 72 and 74 has been obtained. The x-ray is also used to determine whether the downward pressure exerted by the hand brace 44 is properly aligning the bones of the user's hand, wrist, and forearm in the manner shown in FIG. 15. As such, if a determination is made that proper alignment has not been obtained, the pressure exerted by the hand brace 44 is adjusted via the repositioning of the lateral strut 26 and medial strut 28 relative to the threaded members 30. Additionally, in those instances where due to the small size of the user's hand, insufficient downward pressure is applied by the hand brace 44 though the struts 26 and 28 have been moved to their lower-most positions, additional pads may be stacked upon the inner surfaces of adapter pad 84 to exert the necessary pressure.

After the anterior forearm plate 14 and struts 26 and 28 have been properly positioned and proper bone alignment has been achieved, the palm plate 92 is attached to the hand brace 44 by securing the velcro patch 96 of bracket 94 to the velcro patch 98 disposed on the outer surface of lateral member 46. Palm plate 92 is attached to hand brace 44 in a manner wherein the cushioning material 100 included thereon is in firm contact with the palmar surface of the user's hand. After palm plate 92 has been properly positioned, belt member 102 is wrapped about the hand 12 of the user with the extension 106 of belt member 102 being disposed between the thumb and index finger of the user's hand 12. Belt member 102 is maintained in its proper position through the use of the velcro patches 104 contained thereon.

The downward pressure exerted on the second and third metacarpals by the hand brace 44 causes a volar transrelocation as needed to correct a malalignment of the hand or the forearm due to a fracture of the distal radius (i.e. a Colles, fracture), an intercalary carpal instability, or a sub-luxation due to wrist ligament injury. Because the pressure against the metacarpals is constantly maintained, the wrist may be slightly pivoted or rotated without causing further injury to or inhibiting the healing of one of the aforementioned injuries. Indeed, as previously specified, allowing slight movement of the wrist during the healing process aids the healing process. In the initial stages of the healing process, the stop members 76 are positioned in a manner so as to not allow any pivotal movement of the wrist of the user. As the healing process progresses, the positions of stop members 76 may be adjusted so as to permit increasing degrees of flexion and/or extension of the wrist of the user. The use of belt member 102 maintains the adaptor pad 84 of hand brace 44 and the cushioning material 100 of palm plate 92 in firm contact with the hand 12 of the user.

Referring now to FIGS. 9-14, the wrist brace 200 constructed in accordance with the second embodiment of the present invention is depicted. For purposes of illustration, the wrist brace 200 is illustrated in a right arm and hand embodiment which is also adapted to be worn upon the right hand 12 of a user. However, it will be recognized that the invention illustrated in the second embodiment is additionally applicable to left-hand embodiments with the structure of brace 200 being the same but reversed in orientation. In the second embodiment, the wrist brace 200 comprises an anterior forearm plate 202 which has an elongate, generally semi-circular configuration and is positionable adjacent the anterior aspect and lateral and medial sides of the user's forearm. Anterior plate 202 is preferably formed from a relatively thin sheet of plastic material, though other materials are contemplated herein. In the second embodiment, anterior plate 202 is formed in different sizes so as to accommodate the forearms of both adult and adolescent users. Attached to the inner forearm-contacting surface of anterior plate is a layer of foam padding 204 which is used to alleviate discomfort to the user when wearing the wrist brace 200. The wrist brace 200 of the second embodiment is preferably secured to the forearm of the user via one or more strap members 205 rigidly attached to the anterior plate 202 which are extensible about the forearm of the user. As an alternative to the strap members 205, the wrist brace 200 of the second embodiment may include a posterior forearm plate 206 (shown in phantom in FIGS. 9 and 10) which is identically configured to the posterior plate 16 shown and described with respect to the first embodiment. In this regard, the posterior plate 206 is positioned adjacent the posterior aspect of the user's forearm and attached to the anterior forearm plate 202 via strap members 208 rigidly attached thereto, so as to maintain wrist brace 200 upon the user's forearm.

The wrist brace 200 constructed in accordance With the second embodiment further comprises a lateral strut 210 rigidly attached to the lateral side of the anterior forearm plate 202 and a medial strut 212 rigidly attached to the medial side of the anterior forearm plate 202. To facilitate such attachment, disposed within lateral strut 210 are a pair of apertures 214 which are adapted to receive fasteners, such as screws 216. Though not fully shown, medial strut 212 is identically configured to lateral strut 210 and likewise includes fastener receiving apertures therein. In attaching struts 210 and 212 to anterior plate 202, screws 216 extend through anterior plate 202 and are threadably received into threaded grommets 218 disposed underneath the layer of foam padding 204. The reason for using screws 216 to facilitate the attachment of struts 210 and 212 to anterior plate 202 will be explained in greater detail below.

Figures 9, 10:
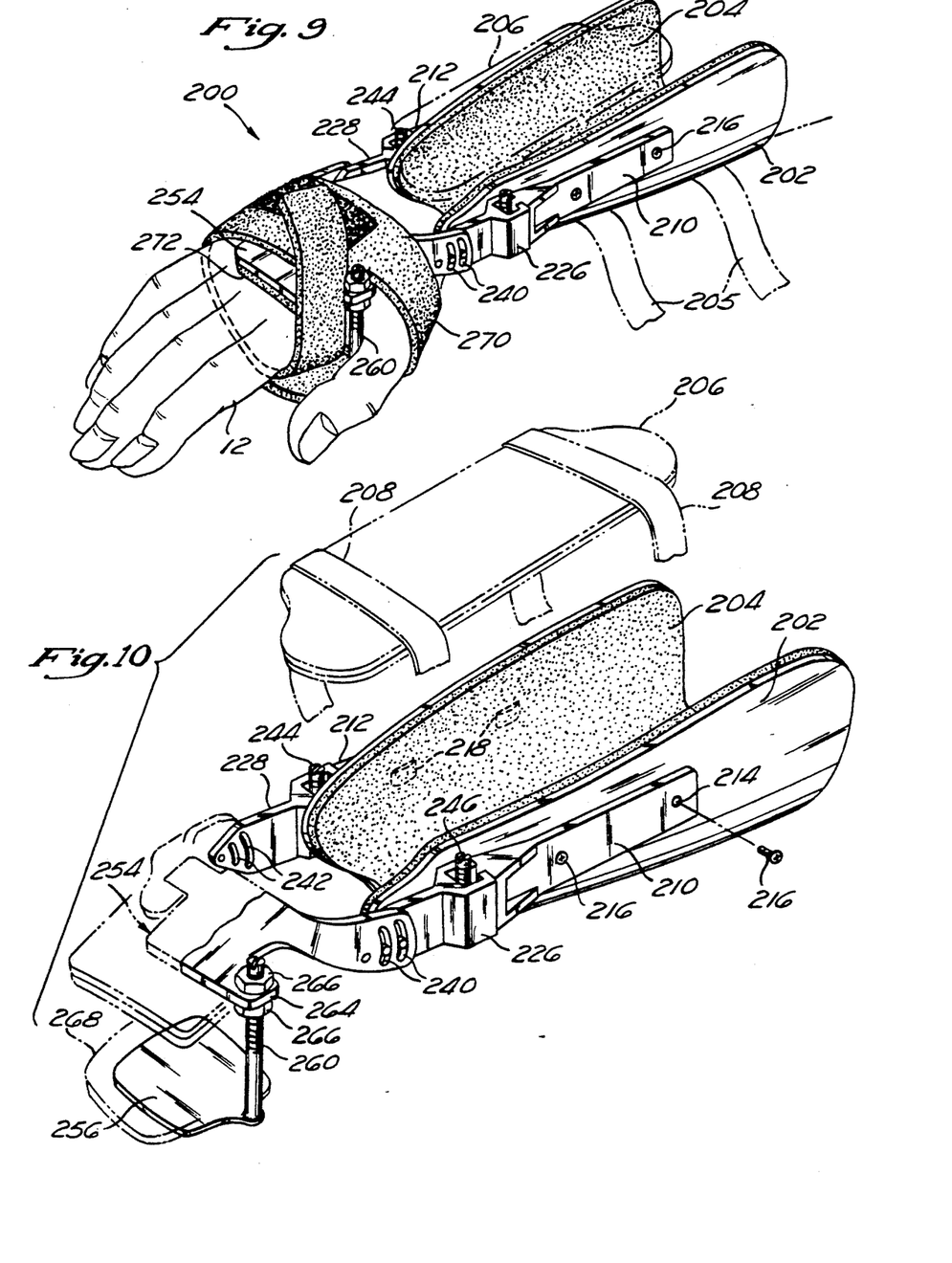
FIG. 9 is a perspective view of a wrist brace constructed in accordance with a second embodiment of the present invention as attached to the arm of a user.
FIG. 10 is a perspective view illustrating the components comprising the second embodiment of the present invention.
Figures 11, 12, 13, 14, 15:
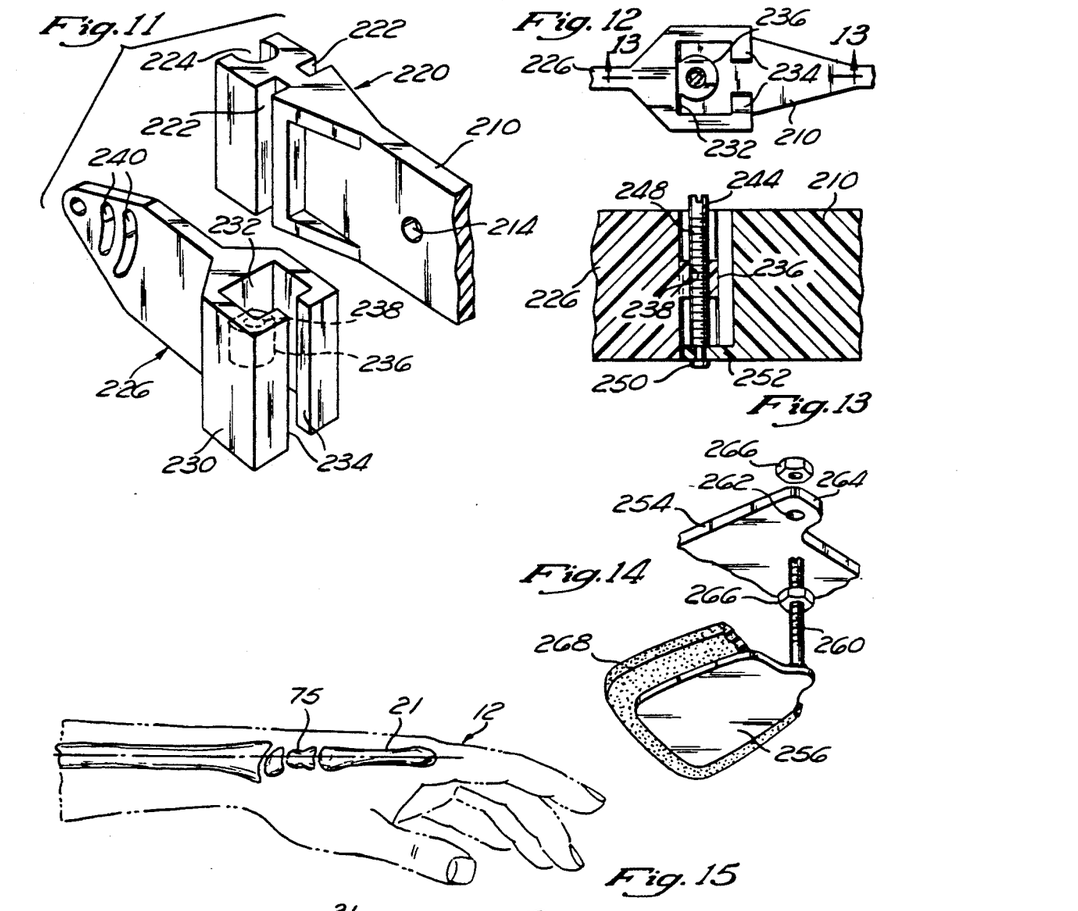
FIG. 11 is a perspective view illustrating the manner in which a connector and strut of the second embodiment are slidably interconnected.
FIG. 12 is a top view illustrating the engagement of a connector and strut of the second embodiment.
FIG. 13 is a cross-sectional view taken along line 13—13 of FIG. 12.
FIG. 14 is a partial perspective view of a palm plate constructed in accordance with the second embodiment of the present invention.
FIG. 15 is a side view of a user's hand, illustrating the bones of the forearm, wrist, and hand in proper alignment.

As previously specified, lateral strut 210 and medial strut 212 are identically configured. In the second embodiment, struts 210 and 212, like anterior plate 202, are preferably formed of plastic, though other materials may be utilized as an alternative. Referring now to FIG. 11, formed on the proximal ends of both the lateral strut 210 and medial strut 212 is a connector portion 220. As seen in FIG. 11, each connector portion 220 comprises an area of increased thickness having a pair of elongate, vertically oriented slots 222 disposed within the opposed sides thereof. Connector portion 220 further defines a vertically oriented groove 224 having a generally semi-circular configuration. It will be recognized that though connector portion 220 is shown as being formed upon lateral strut 210, the connector portion 220 of medial strut 212 is identically configured. Importantly, as seen in FIGS. 9 and 10, lateral strut 210 and medial strut 212 are sized so as not to extend beyond the opposed ends of anterior plate 202 when attached thereto. In this respect, the proximal ends of struts 210 and 212, and more particularly the connector portions 220 thereof, are disposed adjacent the lateral and medial sides of anterior plate 202, near the end thereof which is closest the wrist of the user.

The wrist brace 200 constructed in accordance with the second embodiment of the present invention further comprises a lateral connector 226 and a medial connector 228 which are slidably connected to the connector portions 220 of lateral strut 210 and medial strut 212. Like struts 210 and 212, lateral connector 226 and medial connector 228 are preferably formed from a plastic material and are identically configured. As seen in FIG. 11, lateral connector 226 includes a receiver portion 230 defining a channel 232 which is sized and configured to slidably receive the connector portion 220 of lateral strut 210. As seen in FIG. 12, when connector portion 220 is slidably received into channel 232, the tab members 234 formed on receiver portion 230 are slidably received into the slots 222 disposed within connector portion 220. Additionally, a cylindrical boss 236 formed within channel 232 is slidably received into the groove 224 of channel portion 220. Disposed within boss 236 is an internally threaded aperture 238 which extends axially therethrough, the use of which will be discussed in greater detail below. It will be recognized that though receiver portion 230 has been described with respect to lateral connector 226, the receiver portion of medial connector 228 is identically configured and interfaced to the connector portion 220 of medial strut 212 in the same manner as previously discussed.

Disposed within lateral connector 226 is a first pair of arcuate slots 240, while disposed within medial connector 228 is a second pair of arcuate slots 242. As seen in FIGS. 9 and 10, when lateral connector 226 and medial connector 228 are interfaced to anterior plate 202 via the receipt of the connector portions 220 of struts 210 and 212 into the respective receiver portions 230, each extends forwardly from anterior plate 202 such that the pairs of arcuate slots 240 and 242 are clearly exposed. It will be appreciated that the connector portions 220 of lateral strut 210 and medial strut 212 may have alternative configurations, and that the receiver portions 230 of lateral connector 226 and medial connector 228 may be configured accordingly.

In the second embodiment, the lateral connector 226 and medial connector 228 are selectively positionable relative the connector portions 220 of struts 210 and 212. Such adjustability is facilitated by a first adjustment member 244 and a second adjustment member 246. As seen in FIG. 13, first adjustment member 244 comprises an elongate threaded portion 248 which is threadably received into the aperture 238 disposed within boss 236 of lateral connector 226. Disposed on the lower end of threaded portion 248 is a shoulder 250 which is rotatably received into a wall 252 defining the bottom of groove 224. Due to the threaded interconnection between first adjustment member 244 and lateral connector 226 via the receipt of threaded portion 248 into aperture 238, the rotation of first adjustment member 244 in a first direction will cause lateral connector 226 to move upwardly relative lateral strut 210, while rotation of first adjustment member 244 in a second direction will cause lateral connector 226 to move downwardly relative lateral strut 210. It will be recognized that second adjustment member 246 is identically configured to first adjustment member 244 and includes a threaded portion which is threadably received into the boss formed within medial connector 228. Additionally, second adjustment member 246 is interfaced to medial strut 212 and medial connector 228 in the same manner as previously described. In this respect, by rotating second adjustment member 246, medial connector 228 is upwardly and downwardly movable relative medial strut 212.

The wrist brace 200 of the second embodiment further comprises a hand brace 254 (shown in phantom in FIG. 10) which is similarly configured to and used for the same purposes as the hand brace 44 shown and described in the first embodiment. Though having an overall configuration which is substantially identical to hand brace 44, hand brace 254 does not comprise separate halves, and therefore is not adapted to have its size adjusted. As can be appreciated, since anterior plate 202 is sized to accommodate a particular user's forearm and struts 210 and 212 are rigidly attached to anterior plate 202, no adjustability of hand brace 254 is required. Like hand brace 44, the hand brace 254 includes opposed pairs of arcuate slots which are adapted to be interfaced to the pairs of arcuate slots 242 and 244 such that the receipt of stop members within the aligned pairs of slots may be used to control the flexion and extension of hand brace 254 relative the anterior plate 202. Importantly, the upward and downward adjustability of lateral connector 226 and medial connector 228 allows hand brace 254 to be interfaced to the posterior aspect of the user's hand 12 so as to apply the necessary downward pressure to the second metacarpal bone 21 and third metacarpal bone 23 (as seen in FIG. 8) to achieve a volar transrelocation of the user's wrist to correct the bone malalignment shown in FIG. 16 As with the wrist brace 10 of the first embodiment, the pivot pins used to interconnect the hand brace 254 to lateral connector 226 and medial connector 228 are preferably constructed from a radiopaque material and disposed adjacent opposite sides of the capitate bone 75 of the user's wrist when the wrist brace 200 is attached thereto, for the same reasons as previously discussed.

Previously, numerous references have been made to a volar transrelocation of the user's wrist as caused by the downward pressure exerted by the hand brace 44 or hand brace 254 on the posterior aspect of the user's hand 12, and more particularly, the second metacarpal bone 21 and third metacarpal bone 23. FIG. 15 illustrates the capitate bone 75 and second metacarpal bone 21 of the user's hand 12 in proper alignment. As illustrated in FIG. 16, when the capitate bone 75 and metacarpal bones are forced into an orientation above that which is normal due to a particular wrist injury, a volar transrelocation is needed to push the bones into a normal alignment. As will be recognized, due to the nature of the bone malalignment as shown in FIG. 16, a volar transrelocation requires that a downward pressure be exerted upon the posterior aspect of the user's hand to achieve proper alignment. As such, the hand braces 44 and 254 are adapted to exert such downward pressure. Referring now to FIG. 17, certain wrist injuries cause the capitate bone 75 and metacarpal bones to achieve an orientation below that which is normal. In this particular situation, a dorsal transrelocation is needed to push the wrist bones into a normal alignment. Due to the nature of the bone malalignment shown in FIG. 17, a dorsal transrelocation is facilitated by exerting upward pressure against the palmar surface of the user's hand 12 to achieve a proper alignment.

The wrist brace 10 constructed in accordance with the first embodiment of the present invention is not specifically adapted to cause a dorsal transrelocation so as to correct a malalignment of the bones of the user's wrist as shown in FIG. 17. In this respect, though the hand brace 44 of the first embodiment is adapted to apply downward pressure to the posterior aspect of the user hand 12, the palm plate 92 attached thereto is not adapted to apply upward pressure to the palmar surface of the hand in an amount sufficient to cause a dorsal transrelocation.

The wrist brace 200 constructed in accordance with the second embodiment is specifically configured to selectively initiate both volar and dorsal transrelocations. As previously specified, the hand brace 254 of the second embodiment is adapted to apply downward pressure to the posterior aspect of the user's hand 12, thereby causing a volar transrelocation. To facilitate the application of the upward pressure to the palmar surface of the hand 12 necessary to cause a dorsal transrelocation, a palm plate 256, as seen in FIG. 14, is interfaced to the hand brace 254. In the second embodiment, palm plate 256 includes a threaded member 260 rigidly attached thereto and extending upwardly therefrom. As seen in FIGS. 10 and 14, the distal end of threaded member 260 is adapted to be received into an aperture 262 disposed within an extension 264 formed on and extending outwardly from the hand brace 254. Threaded member 260 is retained within aperture 262 through the utilization of a pair of jam nuts 266. Palm plate 256 further includes a layer of cushioning material 268 attached thereto to provide a padded interface between palm plate 256 and the palmar surface of the user's hand. As will be recognized, the position of palm plate 256 may be adjusted upwardly toward hand brace 254 by selectively positioning the jam nuts 266 along the length of threaded member 260. Thus, palm plate 256 may be caused to exert upward pressure on palmar surface of the user's hand 12 thereby causing a dorsal transrelocation of the bones within the user's hand and wrist. It will be appreciated that palm plate 92 of the first embodiment may be interfaced to hand brace 44 in the same manner as previously described.

As seen in FIG. 9, a strap member 270, identically configured to the strap member 102 described with respect to the first embodiment, is used in conjunction with the wrist brace 200 of the second embodiment. In this respect, strap member 270 is wrapped about the user's hand to maintain the hand brace 254 in abutting contact with the posterior aspect of the user's hand. Additionally, one or more adaptor pads 272 may be releasably attached to the inner surface of hand brace 254 for the same reasons as previously described with respect to the first embodiment.

As previously specified, the lateral strut 210 and medial strut 212 are connected to the anterior plate 202 through the use of screws 216. Advantageously, by removing the corresponding screws from each of the struts and loosening the remaining pair, the struts 210 and 212, and hence the hand brace 254 interfaced thereto, may be pivoted upwardly relative the anterior plate 202. Such pivotal movement allows the wrist brace 200 to be easily interfaced to the arm of the user. In this respect, after the hand brace 254 has been pivoted upwardly, the user's forearm is placed into anterior plate 202 and the hand brace 254 subsequently pivoted downwardly so as to come into abutting contact with the posterior aspect of the user's hand 12. Once hand brace 254 has been brought into contact with the Posterior aspect of the user's hand 12, the removed pair of screws are reinserted and all the screws are tightened.

With the structure defined, the operation of the wrist brace 200 of the present invention may be described. Initially, the corresponding screws 216 within struts 210 and 212 farthest from hand brace 254 are removed and the remaining set of screws 216 are loosened thereby allowing the hand brace 254 to be pivoted upwardly relative the anterior plate 202. Once hand brace 254 has been pivoted upwardly, the user's forearm is placed within the anterior plate 202. The hand brace 254 is then pivoted downwardly so as to be positioned adjacent the posterior aspect of the hand 12. The loosened set of screws are then tightened and the removed set of screws reinserted into their respective struts and tightened. As with the first embodiment, as the initial positioning of the hand brace 254 occurs, the stop members used to interface the hand brace 254 to the lateral connector 226 and medial connector 228 are tightened so as to maintain the hand brace 254 in a fixed, i.e. "neutral", position which is generally parallel to the posterior aspect of the user's hand 12. The anterior plate 202 is retained upon the user's forearm through the utilization of the strap members 205 or the posterior forearm plate 206 and strap members 208 rigidly attached thereto.

Once the wrist brace 200 has been properly secured to the user's forearm, the hand brace 254 is caused to apply downward pressure to the posterior aspect of the user's hand 12 (provided that a volar transrelocation is required) by manipulating the vertical positions of lateral connector 226 and medial connector 228 via first adjustment member 244 and second adjustment member 246, respectively. If necessary, one or more adaptor pads may be attached to the inner surface of the hand brace 254 to aid in exerting such downward pressure. In those situations where a dorsal transrelocation is required, once the hand brace 254 is positioned adjacent the posterior aspect of the user's hand 12, the palm plate 256 is attached thereto in a manner operable to apply the necessary upward pressure to the palmar surface of the user's hand. Importantly, the pivot pins used to interconnect the lateral connector 226 and medial connector 228 to the hand brace 254 are preferably oriented adjacent opposed sides of the capitate bone 75 of the user's wrist for the same reasons as previously discussed with respect to the first embodiment. In this respect, x-ray imaging is used to verify such positioning. In the event only a volar transrelocation is required, the palm plate 256 is still attached to the hand brace 254 to provide support to the palmar surface of the user's hand 12, but is not connected to the hand brace 254 so as to apply upward pressure to the palmar surface.

After the hand brace 254 or palm plate 256 has been properly adjusted to exert the necessary downward or upper pressure, the stop members used to interconnect the lateral connector 226 and medial connector 228 to the hand brace 254 may be manipulated so as to provide limited amounts of flexion and extension of the wrist. Additionally, the strap 270 is placed about the hand brace 254 to maintain it in abutting contact with the user's hand.

Although for purposes of illustration, certain materials, components, and structural embodiments have been depicted, those skilled in the art will recognize that various modifications to the same can be made without departing from the spirit of the present invention, and such modifications are clearly contemplated herein.

What is claimed is:

1. A wrist brace comprising:
   an anterior forearm plate abutted against the anterior aspect of a user's forearm;
   a lateral strut attached to said anterior forearm plate so as to be positioned adjacent the lateral aspect of the forearm;
   a medial strut attached to said anterior forearm plate so as to be positioned adjacent the medial aspect of the forearm;
   a hand brace pivotally connected to the proximal ends of said lateral strut and said medial strut, said hand brace being abutted against the posterior aspect of a user's hand and adapted to selectively apply downward pressure to the second and third metacarpal bones of the user's hand, said hand brace comprising:
      a lateral member having a lateral extension formed thereon which includes a first pair of arcuate slots disposed therein; and
      a medial member slidably connected to said lateral member and having a medial extension formed thereon which includes a second pair of arcuate slots disposed therein, the slidable connection being operable to allow the distance separating said lateral extension and said medial extension to be selectively adjusted;
   a posterior forearm plate releasably attachable to said lateral strut and said medial strut, said posterior forearm plate being abutted against the posterior aspect of the user's forearm when attached to said lateral and medial struts;
   a means associated with said lateral and medial struts for adjusting the distance separating said lateral strut from said medial strut and the distance separating said struts from said anterior forearm plate, said adjusting means being operable to properly align the struts relative the lateral and medial aspects of the forearm and cause the hand brace to be abutted against and apply downward pressure to the posterior aspect of the user's hand;
   a third pair of arcuate slots disposed within the proximal end of said lateral strut and a fourth pair of arcuate slots disposed within the proximal end of said medial strut, said third and fourth pairs of slots being oriented such that when said hand brace is pivotally connected to said struts, said first and third pairs of slots and said second and fourth pairs of slots are in general alignment;
   a first pivot pin connecting said lateral extension to the proximal end of said lateral strut and a second pivot pin connecting said medial extension to the proximal end of said medial strut, said wrist brace being attached to the arm of the user such that said pivot pins are disposed laterally on opposite sides of the capacitate bone of the user's wrist along a single axis;
   wherein the pivotal connection of said hand brace to said struts is adapted to permit controlled pivotal movement of a user's wrist about said single axis.

2. The brace of claim 1 wherein said first pin and said second pin are constructed of a radiopaque material whereby said pins are identifiable in an x-ray.

3. The brace of claim 1 further comprising a first pair of stop members extending through said first and third pairs of aligned slots and a second pair of stop members extending through said second and fourth pairs of aligned slots, said first and second pairs of stop members being operable to control the amount of flexion and extension of said hand brace relative said struts.

4. The brace of claim 1 wherein said lateral strut includes an offset formed therein adapted to clear the trapezium and scaphoid bones of the user's wrist.

5. The brace of claim 1 wherein said adjusting means comprises:
   a first pair of elongate threaded members extending through and interconnecting said anterior forearm plate and said lateral strut; and
   a second pair of elongate threaded members extending through and interconnecting said anterior forearm plate and said medial strut;
   said lateral strut being selectively positionable along the length of said first pair of threaded members and said medial strut being selectively positionable along the length of said second pair of threaded members.

6. The brace of claim 5 wherein said first pair of threaded members extend through a first pair of elongate grooves disposed within said anterior forearm plate and said second pair of threaded members extend through a second pair of elongate grooves disposed within said anterior forearm plate, said first and second pairs of grooves being adapted to permit the positions of said first and second pairs of threaded members to be adjusted inwardly and outwardly relative the forearm.

7. The brace of claim 1 further comprising a palm plate releasably attached to said hand brace in a manner wherein said palm plate is abutted against the palmar surface of the user's hand.

8. The brace of claim 7 further comprising a belt member used to maintain the palm plate in abutting contact with the palmar surface of the user's hand.

9. The brace of claim 1 wherein said posterior forearm plate includes at least one strap member attached thereof to facilitate the attachment of said posterior forearm plate to said lateral strut and said medial strut.

10. The brace of claim 1 further comprising at least one adapter pad releasably attached to said hand brace for providing a padded interface between said hand brace and the posterior aspect of the user's hand.

11. A wrist brace comprising:
    an arcuate anterior forearm plate abutted against the anterior aspect and lateral and medial sides of a user's forearm;
    a lateral strut rigidly attached to a lateral portion of said anterior forearm plate;
    a medial strut rigidly attached to a medial portion of said anterior forearm plate;
    a lateral connector slidably attached to said lateral strut so as to be positioned adjacent the lateral aspect of the user's wrist;
    a medial connector slidably attached to said medial strut so as to be positioned adjacent the medial aspect of the user's wrist;
    a hand brace pivotally connected to said lateral connector and said medial connector, said hand brace being abutted against the posterior aspect of a user's hand and adapted to selectively apply downward pressure to the posterior aspect of the user's hand, said hand brace including a lateral extension formed thereon having a first pair of arcuate slots disposed therein and a medial extension formed thereon having a second pair of arcuate slots disposed therein;

a means associated with said lateral and medial connectors for adjusting the positioning of said connectors relative said struts, said adjusting means being operable to properly align the connectors relative the lateral and medial aspects of the user's wrist and cause the hand brace to be abutted against and apply downward pressure to the posterior aspect of the user's hand;

a third pair of arcuate slots disposed in said lateral connector and a fourth pair of arcuate slots disposed in said medial connector, said third and fourth pairs of slots being oriented such that when said hand brace is pivotally connected to said connectors, said first and third pairs of slots and second and fourth pairs of slots are in general alignment;

a first pivot pin used to connect said lateral extension to said lateral connector and a second pivot pin used to connect said medial extension to said medial connector, said wrist brace being attached to the arm of the user such that said pivot pins are disposed laterally on opposite sides of the capitate bone of the user's wrist along a single axis;

wherein the pivotal connection of said hand brace to said lateral and medial connectors is adapted to permit controlled pivotal movement of the user's wrist about said single axis.

12. The brace of claim 11 wherein said first pin and said second pin are constructed of a radiopaque material whereby said pins are identifiable in an x-ray.

13. The brace of claim 11 further comprising a first pair of stop members extending through said first and third pairs of aligned slots and a second pair of stop members extending through said second and fourth pairs of aligned slots, said first and second pairs of stop members being operable to control the amount of flexion and extension of the hand brace relative said connectors.

14. The brace of claim 11 wherein said adjusting means comprises:

a first elongate threaded member extending through and interconnecting said lateral strut and said lateral connector; and a second elongate threaded member extending through and interconnecting said medial strut and said medial connector;

said lateral connector being selectively positionable along the length of said first threaded member and said medial connector being selectively positionable along the length of said second threaded member.

15. The brace of claim 11 further comprising a palm plate threadably connected to said hand brace in a manner wherein said palm plate is abutted against and selectively operable to apply upward pressure to the palmar surface of the user's hand.

16. The brace of claim 15 further comprising a belt member used to maintain the hand brace in abutting contact with the posterior aspect of the user's hand.

17. The brace of claim 11 further comprising a posterior forearm plate releasably attachable to said anterior forearm plate, said posterior forearm plate being abutted against the posterior aspect of the forearm.

18. The brace of claim 12 wherein said posterior forearm plate includes at least one strap member attached thereto to facilitate the attachment of said posterior forearm plate to said anterior forearm plate.

19. The brace of claim 11 further comprising at least one strap member rigidly attached to said anterior forearm plate and extensible about the user's forearm for securing the wrist brace thereto.

20. The brace of claim 11 further comprising at least one adapter pad releasably attachable to said hand brace for providing a padded interface between said hand brace and the anterior aspect of the user's hand.

* * * * *